United States Patent
Cottam et al.

(10) Patent No.: US 6,696,441 B1
(45) Date of Patent: Feb. 24, 2004

(54) INHIBITION OF P53-INDUCED STRESS RESPONSE

(75) Inventors: Howard B. Cottam, Escondido, CA (US); Lorenzo M. Leoni, San Diego, CA (US); Dennis A. Carson, Del Mar, CA (US)

(73) Assignee: The Regents of the University of California, Oakland, CA (US)

( * ) Notice: Subject to any disclaimer, the term of this patent is extended or adjusted under 35 U.S.C. 154(b) by 70 days.

(21) Appl. No.: 09/637,531

(22) Filed: Aug. 11, 2000

(51) Int. Cl.[7] .................. A61K 31/425; A61K 31/42; A61K 31/555; C07D 513/12; C07D 401/14

(52) U.S. Cl. .............. 514/233.2; 514/322; 514/368; 514/375; 544/115; 546/199; 546/270.4; 546/273.1; 546/274.1; 548/151; 548/368; 548/218

(58) Field of Search ................ 548/154, 151, 548/218; 546/199, 270.4, 273.1, 774.1; 544/115; 514/233.2, 322, 368, 375

(56) References Cited

U.S. PATENT DOCUMENTS

| | | | |
|---|---|---|---|
| 4,559,157 A | 12/1985 | Smith et al. | 252/90 |
| 4,608,392 A | 8/1986 | Jacquet et al. | 514/844 |
| 4,820,508 A | 4/1989 | Wortzman | 424/59 |
| 4,938,949 A | 7/1990 | Borch et al. | 424/10 |
| 4,992,478 A | 2/1991 | Geria | 514/782 |
| 5,696,260 A | 12/1997 | Shaw et al. | 544/115 |

FOREIGN PATENT DOCUMENTS

| | | | | |
|---|---|---|---|---|
| JP | 11029475 | 2/1999 | ......... | A61K/31/425 |
| JP | 1110630 | 4/1999 | ......... | A61K/31/425 |
| JP | 11-106340 | 4/1999 | ......... | A61K/31/425 |
| WO | 99/16790 | 4/1999 | ........... | C07K/14/47 |
| WO | 99/41985 | 8/1999 | ......... | A01N/37/18 |
| WO | 99/47643 | 9/1999 | ........... | C12N/5/00 |
| WO | 00/44364 | 8/2000 | ......... | A61K/31/00 |

OTHER PUBLICATIONS

Burnett, J.C., et al., "Atrial Natriutetic Peptide Elevation in Congestive Heart Failure in the Human", *Science*, 231, pp. 1145–1147, (Mar. 7, 1986).

Burnett, J.C., et al., "Effects of synthetic atrial natriuretic factor on renal function and renin release", *American Journal of Physiology: Renal, Fluid and Electrolyte Physiology*, 16 (5), pp. F863–F866, (Nov. 1984).

Cordon–Cardo, C., et al., "Genetic Studies and Molecular Markers of Bladder Cancer", *Seminars in Surgical Oncology*, 13 (5), pp. 319–327, (1997).

Donehower, L.A. et al., "Mice Deficient For p53 Are Developmentally Normal But Susceptible to Spontaneous Tumours", *Nature*, 356, pp. 215–221, (Mar. 19, 1992).

Ermolaeva, V.G., et al., "Synthesis and Tuberculostatic Activity of Certain Heterocyclic Substituted Arylthioureas", Translated from: *Khimiko–Farmatsaevticheskii Zhurnal*, No. 1, Original article submitted Jun. 16, 1966., pp. 17–19, (Jan. 1967).

Gottlieb, T.M., et al., "p53 in Growth Conrtol and Neoplasia", *Biochimica et Biophysica Acta, 1287*, pp. 77–102, (1996).

Hendry, J.H., et al., "P53 deficiency produces fewer regenerating spermatogenic tubules after irradiation", *Int. J. Radiat. Biol.*, 70 (6), pp. 677–682, (1996).

Jacks, T., et al., "Tumor Spectrum Analysis in p53–Mutant Mice", *Current Biology*, 4 (1), pp. 1–7, (1994).

Komarov, P.G., et al., "A Chemical Inhibitor of p53 That Protects Mice from the Side Effects of Cancer Therapy", *Science*, 285, pp. 1733–1737, (Sep. 10, 1999).

Komarova, E.A., et al., "Could p53 be a target for therapeutic suppresion?", *Seminars in Cancer Biology*, 8 (5), Article No. se980101, pp. 389–400, (1998).

Komarova, E.A., et al., "Transgenic mice with p53–responsive lacZ: p53 activity varies dramatically during normal development and determines radiation and drug sensitivity in vivo", *The EMBO Journal*, 16 (6), pp. 1391–1400, (1997).

Levine, A.J., et al., "The 1993 Walter Hubert Lecture: The role of the p53 tumour–suppressor gene in tumorigenesis", *British Journal of Cancer*, 69 (3), pp. 409–416, (1994).

Rogel, A., et al., "p53 Cellular Tumor Antigen: Analysis of mRNA Levels in Normal Adult tissues, Embryos, and Tumors", *Molecular and Cellular Biology*, 5 (10), pp. 2851–2855, (1985).

Schmid, P., et al., "Expression of p53 during mouse embryogenesis", *Development*, 113 (3), pp. 857–865, (Nov. 1991).

Schwartz, D., et al., "Expression of p53 Protein in Spermatogenesis is Confined to the Tetraploid Pachytene Primary Spermatocytes", *Oncogene*, 8 (6), pp. 1487–1494, (Jun. 1993).

Singh, A., et al., "Heterocyclic Systems Containing Bridgehead Nitrogen Atom: Part XXV—Syntheses of Imidazo [2,1–b] benzothiazoles & Quinaxlino–[2,3:4',5']imidazo[2', 1'–b]benzothiazoles", *Indian Journal of Chemistry, 14B* (7), pp. 997–998, (Dec. 1976).

(List continued on next page.)

*Primary Examiner*—Alan L. Rotman
*Assistant Examiner*—Raymond Covington
(74) *Attorney, Agent, or Firm*—Schwegman, Lundberg, Woessner & Kluth, P.A.

(57) ABSTRACT

The present invention provides compounds that act to suppress p53 activity in mammalian cells, and a method to effectively suppress p53 activity in the cells of a mammal subject to a stress or pathology that is ameliorated by such suppression.

9 Claims, 3 Drawing Sheets

OTHER PUBLICATIONS

Steele, R., et al., "The p53 Tumour Suppressor Gene", *British Journal of Surgery, 85* (*11*), pp. 1460–1467, (1998).

Tron, V.A., et al., "p53–Regulated Apoptosis Is Differentiation Dependent in Ultraviolet B–Irradiated Mouse Keratinocytes", *American Journal of Pathology, 153* (*2*), pp. 579–585, (Aug. 1998).

Gineinah, M.M., et al., "Sythesis and antiinflammatory evaluation of new 2– and 3–substituted 1,2, 4–triazolo (4,3–c and [1, 5–c] quinazoline derivatives", *Database Registry file on STN* (Columbus, OH, USA) No. 13422676, *Med. Chem. Res. 2000, 10*(*4*), 243–252, (2000).

Hu, M.K., et al., "Guanidine–annelated heterocycles XIII", *Database Registry file on STN* (Columbus, OH) No. 115–71526, (Feb. 1991).

INHIBITION OF P53-INDUCED STRESS RESPONSE

GOVERNMENT FUNDING

The invention described herein was made with Government support under Grant Numbers GM23200 and CA81534 awarded by the National Institutes of Health. The United States Government has certain rights in the invention.

BACKGROUND OF THE INVENTION

Currently, there is a need for novel, potent, and selective agents to prevent detrimental effects upon cells due to DNA damage, such as caused by chemotherapy, radiation, ischemic event, including ischemia-reperfusion injury and organ transplantation, and the like. There is also a need for pharmacological tools for the further study of the physiological processes associated with intracellular DNA damage.

p53, the product of the p53 tumor suppressor gene, is a multifunctional tumor suppressor protein, involved in the negative control of cell growth. In response to a variety of stressors, p53 induces growth arrest or apoptosis, thereby eliminating damaged and potentially dangerous cells. T. M. Gottleib et al., *Biochim. Biophys, Acta,* 1287, 77 (1996). Mutations in the p53 gene are frequently associated with the metastatic stage of tumor progression, and lack of functional p53 is accompanied by rapid tumor progression, resistance to anti-cancer therapy and increased tumor angiogenesis. See, e.g., A. J. Levine et al., *Br. J. Cancer,* 69, 409 (1994); R. J. Steele et al., *Br. J. Surg.,* 85, 1460 (1998); C. Cordon-Cardo et al., *Surg. Oncol.,* 13, 319 (1997). p53 deficiency in mice is associated with a high frequency of spontaneous cancers. L. A. Donehower et al., *Nature,* 356, 215 (1992); T. Jacks et al., *Curr. Biol.,* 4, 1 (1994). On the basis of these reports, the inactivation of p53 was viewed as an unfavorable event, and it has been speculated that cancer can be inhibited by restoration of p53 function.

However, in mice, the level of expression of p53 has been reported to be directly related to the susceptibility of normal tissues such as hematopoietic cells, intestinal epithelia and the testis, to damage by anti-cancer therapy. A. Rogel et al., *Mol. Cell, Biol.,* 5, 2851 (1985); P. Schmidt et al., *Development,* 113, 857 (1991), D. Schwartz et al., *Oncogene,* 8, 1487 (1993). p53-dependent apoptosis occurs in such sensitive tissues shortly after gamma-irradiation, and p53-deficient mice survive higher doses of irradiation than do wild-type animals. E. Komarov et al., *EMBO J.,* 16, 1391 (1997); J. H. Hendry et al., *J. Radiat, Biol.,* 70, 677 (1996); V. A. Tron et al., *Am. J. Pathol,* 153, 579 (1998). These data indicate that p53 is a determinant of the toxic side effects of anti-cancer therapy, and thus may be an appropriate target for suppression, which in turn, may reduce the damage to normal tissues. See, E. A. Komarov et al., *Semin. Cancer Biol.,* 8, 389 (1998).

Recently, P. G. Komarov et al., *Science,* 285, 1733 (1999), reported that a compound of formula:

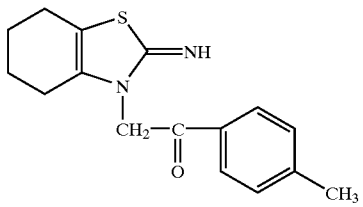

which they named PFTα, protected mice from lethal genotoxic stress associated with 6–8 Gy of gamma radiation, without itself promoting the formation of tumors or affecting the sensitivity of the tumors to radiation. These authors suggested that PFTα might be useful to reduce the side effects of radiation therapy or chemotherapy for human cancers. PFTα is a known 2-imino-tetrahydro-benzothiazole that was first prepared by A. Singh et al., *Ind. J. Chem.,* 1413, 997 (1976) as a potential antihelminthic agent. However, a continuing need exists for compounds that can protect mammalian cells from the damaging effects of chemotherapy and irradiation, or in other situations in which it is desirable to protect tissue from the consequences of clinical or environmental stress.

SUMMARY OF THE INVENTION

The present invention provides compounds that act to suppress p53 activity in mammalian cells, and a method to effectively suppress p53 activity in the cells of a mammal subject to a stress or pathology that is ameliorated by such suppression. Accordingly, there is provided a method of p53 suppression comprising administering to a mammal in need of said suppression an effective amount of a compound of formula (I):

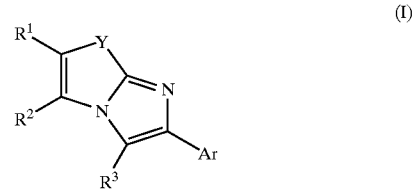

wherein $R^1$, $R^2$ and $R^3$ are independently hydrogen, halo, hydroxy, cyano, $N(R_a)(R_b)$, $S(R_a)$, $NO_2$, $(C_1-C_6)$alkyl, $(C_1-C_6)$alkoxy, $(C_2-C_6)$alkynyl, $(C_2-C_6)$alkenyl, $(C_2-C_7)$alkanoyl, $(C_2-C_7)$alkanoyloxy, or $(C_3-C_7)$cycloalkyl or $R^1$ and $R^2$ taken together are benzo, optionally substituted by $R^1$, $(C_3-C_5)$alkylene or methylenedioxy; wherein $R_a$ and $R_b$ are each independently hydrogen, $(C_1-C_3)$alkyl, $(C_2-C_4)$alkanoyl, phenyl, benzyl, or phenethyl; or $R_a$ and $R_b$ together with the nitrogen to which they are attached are a 5–6 membered heterocyclic ring, preferably a pyrrolidino, piperidino or morpholino ring;

Ar is aryl or heteroaryl, optionally substituted with 1–5, preferably 1–2, halo, $CF_3$, hydroxy, CN, $N(R_a)(R_b)$, $(C_1-C_6)$alkyl, $(C_1-C_6)$alkoxy, $(C_2-C_7)$alkanoyl, $(C_2-C_7)$alkanoyloxy, $(C_3-C_7)$cycloalkyl, $(C_2-C_6)$alkanoyl, $(C_2-C_6)$alkenyl, or phenyl.

Y is oxy (—O—), $S(O)_{0-2}$, $C(R^1)(R^3)$, $N(R_a)$, or —P—; or a pharmaceutically acceptable salt thereof.

The invention also provides novel p53 suppressor compounds, as well as pharmaceutical compositions comprising novel compounds of formula I, or a pharmaceutically acceptable salt thereof, in combination with a pharmaceutically acceptable diluent or carrier. Such compounds can be represented by compounds of formula (I), with the proviso that when Y is S, Ar is not phenyl ($C_6H_5$).

Additionally, the invention provides a therapeutic method for preventing or treating a pathological condition or symptom in a mammal, such as a human, wherein the activity of p53 is implicated and antagonism or suppression of its action is desired, comprising administering to a mammal in need of such therapy, an effective amount of a compound of formula (I), or a pharmaceutically acceptable salt thereof. Such pathological conditions or symptoms include blocking, moderating or reversing the deleterious effects of chemotherapeutic agents, particularly those which damage DNA; radiation, particularly radiation therapy (gamma-, beta- or UV-radiation), ischemic event, including stroke, infarct, ischemia-reperfusion injury and ischemia due to organ, tissue or cell transplantation; environmental pollution or contamination and the like.

The invention provides a compound of formula (I) for use in medical therapy as well as the use of a compound of formula (I) for the manufacture of a medicament for the treatment of a pathological condition or symptom in a mammal, such as a human, which is associated with p53-induced cellular damage, i.e., with unwanted apoptosis.

The invention also includes a method for binding a compound of formula (I) to cells and biomolecules comprising p53 receptors, in vivo or in vitro, comprising contacting said cells or biomolecules with an amount of a compound of formula (I) effective to bind to said receptors. Cells or biomolecules comprising ligand-bound p53 receptor sites can be used to measure the selectivity of test compounds for specific receptor subtypes, or can be used as a tool to identify potential therapeutic agents for the treatment of diseases or conditions associated with p53 activation, by contacting said agents with said ligand-receptor complexes, and measuring the extent of displacement of the ligand and/or binding of the agent, by methods known to the art.

As used herein, the term "p53" or "p53 activity" refers to p53 protein. The invention is believed to work by temporarily suppressing expression of the p53 gene and/or activity of p53 protein.

DETAILED DESCRIPTION

Figure 1A:
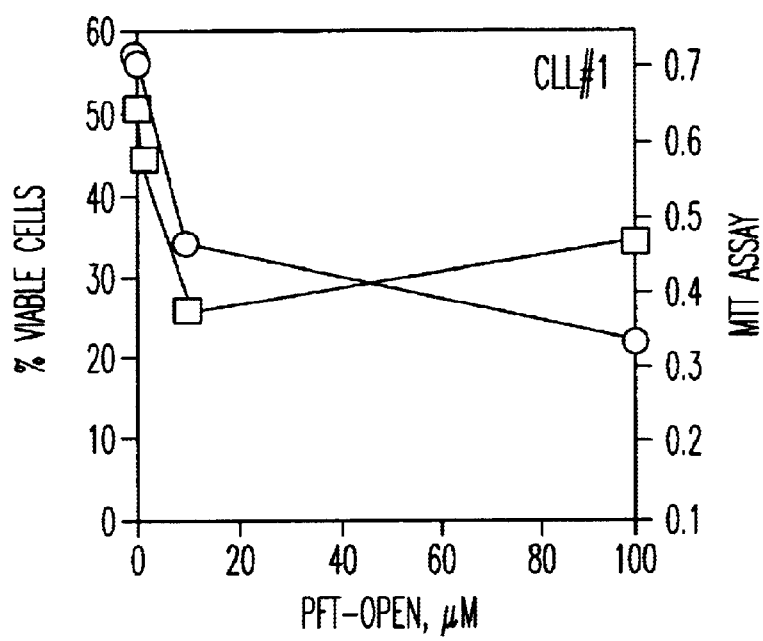
FIG. 1 depicts the effects of IBT and PFT α on B-CLL viability.
Figure 1B:
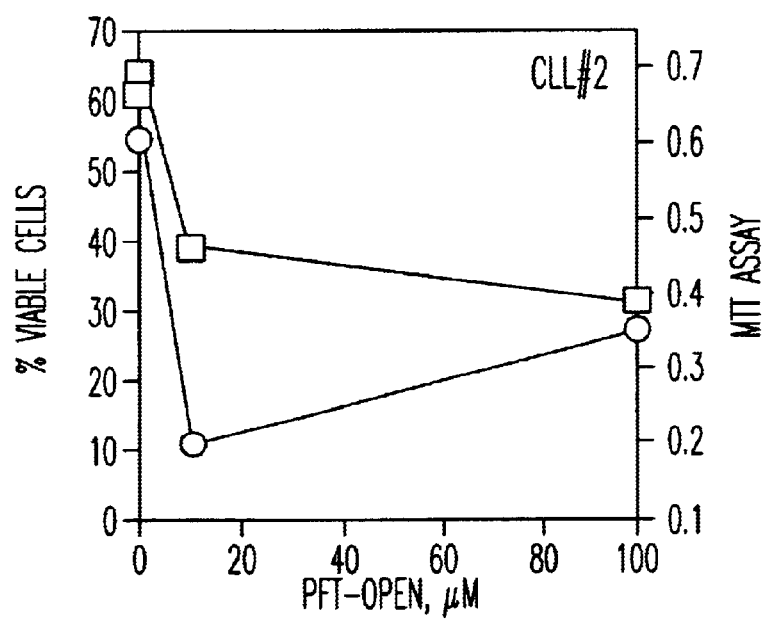
Figure 1C:
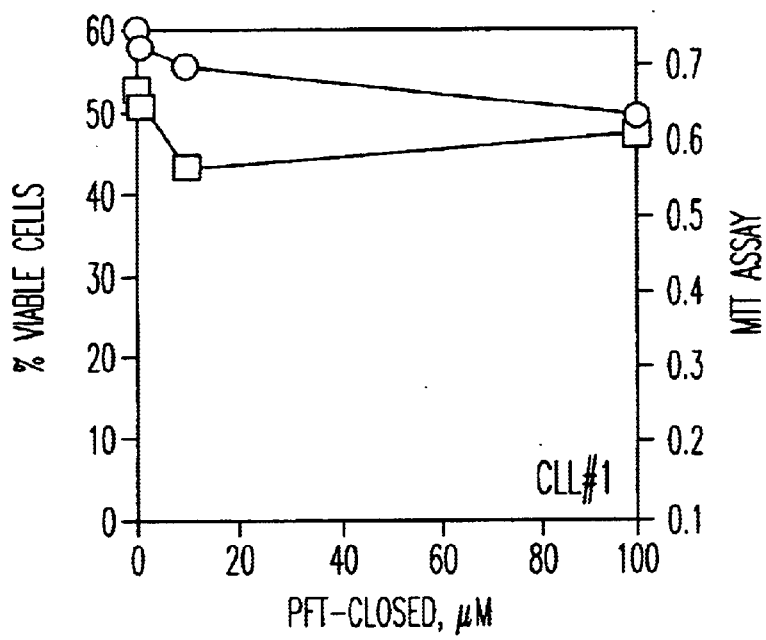
Figure 1D:
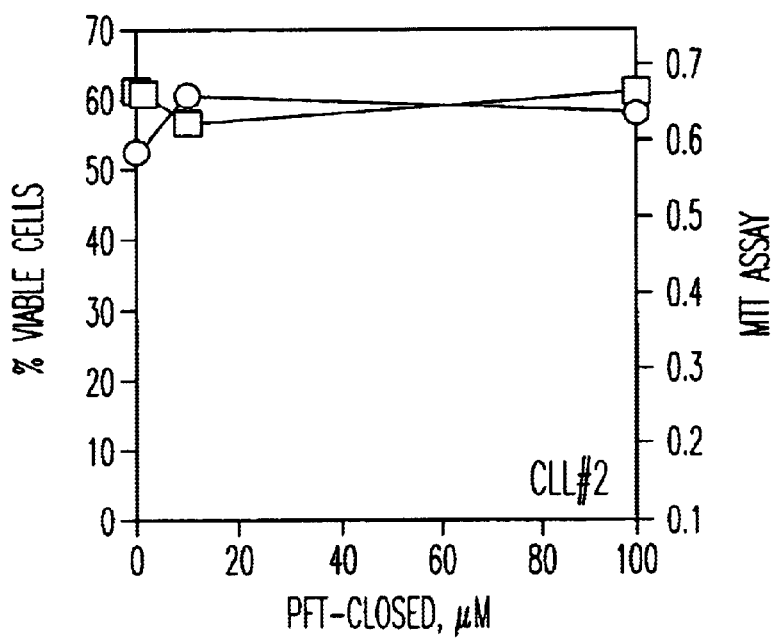

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring nitrogen or carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$–$C_4$)alkyl, phenyl or benzyl. Heteroaryl also includes a radical of an ortho-fused bicyclic heterocycle of about eight to ten ring atoms, particularly a benz-derivative or one derived by fusing a propylene, trimethylene, or tetramethylene diradical thereto. Preferred heteroaryls include pyridin-4-yl and thiophen-2-yl.

It will be appreciated by those skilled in the art that compounds of the invention having a chiral center may exist in and be isolated in optically active and racemic forms. Some compounds may also exhibit polymorphism. It is to be understood that the present invention encompasses any racemic, optically active, polymorphic, or steroisomeric form, or mixtures thereof, of a compound of the invention, which possess the useful properties described herein, it being well known in the art how to prepare optically active forms (for example, by resolution of the racemic form by recrystallization techniques, by synthesis from optically active starting materials, by chiral synthesis, or by chromatographic separation using a chiral stationary phase) and how to determine p53 suppression activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, ($C_1$–$C_6$)alkyl can be methyl, ethyl, propyl, isopropyl, butyl, iso-butyl, sec-butyl, pentyl, 3-pentyl, or hexyl; ($C_3$–$C_7$)cycloalkyl can be cyclopropyl, cyclobutyl, cyclopentyl, or cyclohexyl; the term cycloalkyl includes (cycloalkyl)alkyl of the designated number of carbon atoms; ($C_3$–$C_5$)cycloalkyl($C_2$–$C_4$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylmethyl; ($C_1$–$C_6$)alkoxy can be methoxy, ethoxy, propoxy, isopropoxy, butoxy, iso-butoxy, sec-butoxy, pentoxy, 3-pentoxy, or hexyloxy; ($C_2$–$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$–$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_2$–$C_7$)alkanoyl can be acetyl, propanoyl or butanoyl; halo($C_1$–$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$–$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$–$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$–$C_6$)alkylthio can be methylthio, ethylthio, propylthio, isopropylthio, butylthio, isobutylthio, pentylthio, or hexylthio; ($C_2$–$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ and $R^2$ together is butylene or benzo.

A specific value for $R^3$ is H.

A specific value for Ar is phenyl, 4-pyridyl or 2-thienyl.

A specific value for Y is S, O, $N(R_a)$ or P.

A specific value for $N(R_a)(R_b)$ is amino.

A specific value for halo is Br or F.

Processes for preparing compounds of formula (I) are provided as further embodiments of the invention and are illustrated by the procedures disclosed below in which the meanings of the generic radicals are as given above unless otherwise qualified.

Intermediates useful for preparing compounds of formula (I), are also within the scope of the present invention.

The present invention is based on the discovery that PFTα is both cytotoxic to mammalian cells and unstable in aqueous solution under in vivo conditions. PFT-α undergoes spontaneous ring closure in protic solvents, such as alkanols, to form the imidazo[2,1-b]benzothiazole derivative, abbreviated IBT, as shown in Scheme 1.

Scheme 1

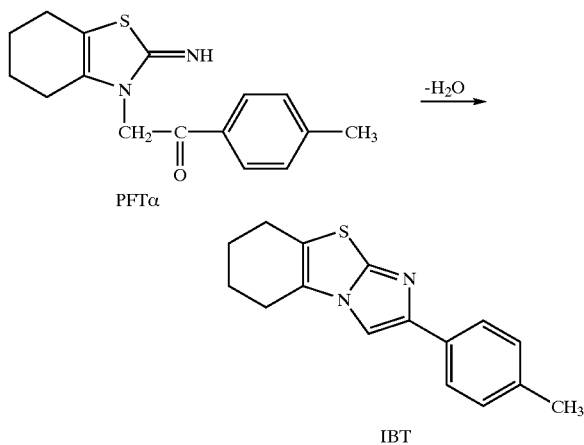

Biological evaluation, described below, demonstrated that IBT is actually responsible for the observed p53 inhibition observed by Komarov et al. (*Science*, 285, 1733 (1999)). Thus, since IBT and compounds of formula (I) are expected to be both less toxic and more stable than imino compounds such as PFT-α, they are desirable agents for protection of mammalian cells against a wide variety of stressors, including therapeutic agents, and clinical and environmental trauma.

Compounds of formula (I) can be readily prepared as disclosed by Singh et al., *Indian J. Chem.*, 7, 997 (1996), as shown in Scheme 2.

Scheme 2

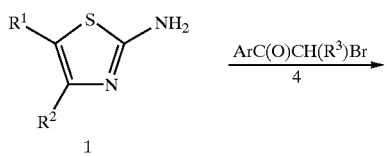

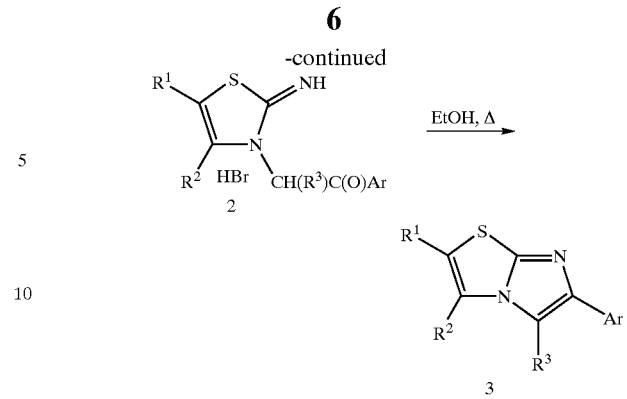

The reaction of 1 and 4 can be carried out simply by combining the compounds in a suitable aprotic solvent such as benzene. See, I. Soldabols et al., *Khim, Pharm, Zh.*, 1, 17 (1967). The conversion of 1→3 can also be accomplished in one step by refluxing 1 and the phenacyl bromide 4 in ethanol. Singh et al. used starting materials wherein $R^1$ and $R^2$ together are —$CH_2)_4$— or —$CH(CH_3)$—$(CH_2)_3$— and Ar is substituted phenyl. Recently, Sumitomo Pharmaceutical Co. Ltd. (Japanese Pat. No. 11-29475) (1999)) disclosed the preparation of certain compounds of formula 2, wherein $R^3$ is H and Ar is substituted phenyl, and Japanese Pat. No. 11-106340 (1999) disclosed the preparation of certain compounds of formula 3 wherein Ar is substituted phenyl or napthyl and $R_1$ and $R^2$ can be, inter alia, H, alkylene or benzo. Compounds of formula 1 were prepared according to Scheme 3.

Scheme 3

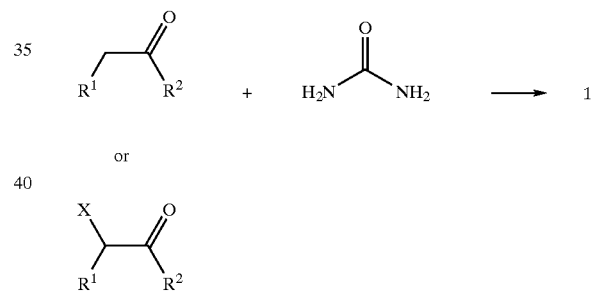

The compounds of formula (I) are disclosed to be useful for "the treatment and prevention of allergic disease and parasitic infectious diseases, or the like."

Certain of the compounds of formula (I) are useful as intermediates to prepare other compounds of formula (I), as would be recognized by the art.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula (I) can be formulated as pharmaceutical compositions and administered to a mammalian host, such as a human patient, such as a cancer patient or patient undergoing organ or tissue transplantation, in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glycerol esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelation.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula (I) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form, for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator or by application of a plurality of drops into the eye.

The ability of a compound of the invention to act as a suppressor of p53 activity may be determined using pharmacological models which are well known to the art, e.g., as disclosed by P. G. Komarov et al., *Science*, 285 1733 (1999).

The invention will now be illustrated by the following non-limiting Examples.

EXAMPLE 1

Ring-closure of PFT-α

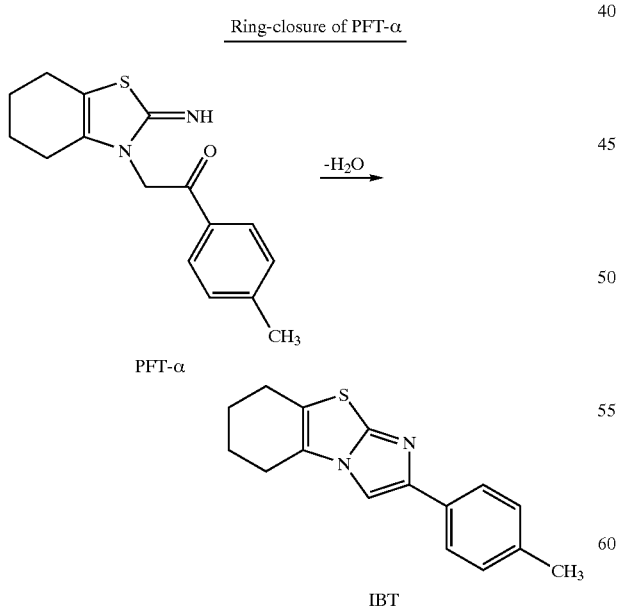

The preparation of PFT-α was accomplished as shown in Scheme 1 by reacting 4-methyl-2-bromoacetophenone with 2-amino-4,5,6,7-tetrahydro-benzothiazole. Upon recrystallization of the PFT-α from isopropyl alcohol, it was noticed that PFT-α readily ring-closed completely to the imidazo[2,1-b]benzothiazole (IBT). Therefore, a subsequent investigation was undertaken to study the propensity of PFT-α to ring-close in protic solvents. Initial results indicated that PFT-α begins cyclizing at room temperature immediately upon dissolution in protic solvents. Thus, PFT-α was dissolved in DMSO and water dilutions were made from this stock. Reversed phase HPLC analysis of the solution at 25° C. over time gave results as shown in Table 1.

TABLE 1

| Time (h) | % cyclized to IBT |
| --- | --- |
| 0 | 5 |
| 18 | 28 |
| 48 | 42 |

In addition, nmr studies were used to confirm the structure of the known IBT and a time course in DMSO-d6 also showed spontaneous conversion of PFT-α to IBT, as judged by the appearance of a new aromatic proton signal at $\delta 8.50$ ppm in the proton spectrum corresponding to the $C_3H$ proton.

This observation brings into question the investigations reported recently by P. G. Komarov et al., *Science*, 285, 1733 (1999) reporting the inhibition of p53 by PFTα. It is likely that the p53 inhibition reported by these investigators was due to IBT and not PFT-α. It is likely that IBT was already present in the treatment solutions and that IBT is actually responsible for the observed p53 inhibition.

EXAMPLE 2

Effect of the p53 Inhibitory Compounds on B-CLL Viability

The malignant lymphocytes from two patients with chronic lymphocytic leukemia [CLL] were isolated by ficoll-hypaque sedimentation and suspended at a density of 1 million cells per milliliter in RPMI 1640 medium supplemented with 10% fetal bovine serum. Two hundred microliter aliquots of cells were dispersed in the wells of culture plates containing the indicated final concentrations of either PFT-α ("PFT-open") or IBT (PFT-closed). After 3 days culture, viable cells were enumerated by fluorescence-activated cell sorting [FACS] after staining with propidium iodide [PI]. Viable cells excluded the dye [open circles]. In addition, cell metabolism was assessed by the ability of the cells to exclude the tetrazolium dye MTT [closed squares]. As shown in FIG. 1, the PFT-open dose-dependently reduced CLL survival, whereas PFT-closed [i.e., IBT] was non-toxic at concentrations up to 100 micromolar.

EXAMPLE 3

Protection Against Spontaneous Apoptosis and Apoptosis Induced by the Anti-metabolite Fludarabine Chronic lymphocytic leukemia [CLL] cells were cultured for 3 days as described in Example 2. Some of the cultures were supplemented with one micromolar of PFT-open or PFT-closed, as indicated. In the experiment shown in the bottom panel of FIG. 2, some of the cultures also contained the cytotoxic adenine nucleoside analog fludarabine [abbreviated F-AraA]. Fludarabine is the first line treatment for CLL, and the toxicity of the drug is dependent upon the p53 pathway. To assess healthy, viable cells, staining was done with both PI, as indicated in Example 2, and with the mitochondrial dye DiOC6. Cells that were both PI negative and DIOC6 high were enumerated by FACS. While PFT-α and IBT exhibited nearly equivalent effects on untreated CLL cells, IBT exerted less protective effects when combined with CLL cells treated with F-AraA than did PFT-α.

EXAMPLE 4

The following illustrate representative pharmaceutical dosage forms, containing a compound of formula (I), for therapeutic or prophylactic use in humans.

| (i) Table 1 | mg/tablet |
|---|---|
| Compound of Formula (I) | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Table 2 | mg/tablet |
|---|---|
| Compound of Formula (I) | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound of Formula (I) | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound of Formula (I) | 1.0 |
| Dibasic sodium phosphate | 12.0 |
| Monobasic sodium phosphate | 0.7 |
| Sodium chloride | 4.5 |
| 01 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| Compound of Formula (I) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| -continued | |
|---|---|
| (vi) Aerosol | mg/can |
| Compound of Formula (I) | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

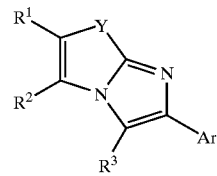

wherein $R^3$ is hydrogen, halo, hydroxy, cyano, $N(R_a)(R_b)$, $S(R_a)$, $NO_2$, $(C_1-C_6)$alkyl, $(C_1-C_6)$alkoxy, $(C_2-C_6)$alkynyl, $(C_2-C_6)$alkenyl, $(C_2-C_7)$alkanoyl, $(C_2-C_7)$alkanoyloxy, or $(C_3-C_7)$cycloalkyl and $R^1$ and $R^2$ taken together are benzo or butylene, optionally substituted by $R^3$, $(C_3-C_5)$alkylene or methylene dioxy; wherein $R_a$ and $R_b$ are each independently hydrogen, $(C_1-C_3)$ alkyl, $(C_2-C_4)$alkanoyl, phenyl, benzyl, or phenethyl;

or $R_a$ and $R_b$ together with the nitrogen to which they are attached are a 5–6 membered heterocyclic ring, preferably a pyrrolidino, piperidino or morpholino ring;

Ar is heteroaryl, optionally substituted with 1–5 halo, $CF_3$, hydroxy, CN, $N(R_a)(R_b)$, $(C_1-C_6)$alkyl, $(C_1-C_6)$ alkoxy, $(C_2-C_7)$alkanoyl, $(C_2-C_7)$alkanoyloxy, $(C_3-C_7)$cycloalkyl, $(C_2-C_6)$alkanoyl, $(C_2-C_6)$alkenyl, or phenyl;

Y is oxy $S(O)_{0-2}$;

or a pharmaceutically acceptable salt thereof.

2. The compound of claim 1 wherein $R^1$ and $R^2$ together is butylene.

3. The compound of claim 1 wherein $R^3$ is H.

4. The compound of claim 1 wherein Ar is 4-pyridyl or 2-thienyl.

5. The compound of claim 1 wherein $N(R_a)(R_b)$ is amino.

6. The method of claim 1 wherein halo is Br or F.

7. The compound of claim 1 wherein $R^1$ and $R^2$ together is benzo.

8. The compound of claim 4 wherein Ar is 4-pyridyl.

9. The compound of claim 4 wherein Ar is 2-thienyl.

* * * * *

UNITED STATES PATENT AND TRADEMARK OFFICE
CERTIFICATE OF CORRECTION

PATENT NO. : 6,696,441 B1
APPLICATION NO. : 09/637531
DATED : February 24, 2004
INVENTOR(S) : Cottam et al.

It is certified that error appears in the above-identified patent and that said Letters Patent is hereby corrected as shown below:

On Title Page, in field (56), under "Other Publications", in column 1, line 1, delete "Natriutetic" and insert -- Natriuretic --, therefor.

On Title Page, in field (56), under "Other Publications", in column 1, line 11, after "L.A." insert -- , --.

On Title Page, in field (56), under "Other Publications", in column 2, line 6, delete "Conrtol" and insert -- Control --, therefor.

Title Page, in field (56), under "Other Publications", in column 2, line 18, delete "suppresion" and insert -- suppression --, therefor.

title page, in field (56), under "Other Publications", in column 2, line 40, delete "Quinaxlino" and insert -- Quinxalino --, therefor.

On title page, in field (56), under "Other Publications", in column 2, line 1, delete "Sythesis" and insert -- Synthesis --, therefor.

On title page, page 2 in field (56), under "Other Publications", in column 2, line 3, delete "(4,3-c" and insert -- [4,3-c] --, therefor.

In column 1, line 34, delete "Biophys," and insert -- Biophys. --, therefor.

In column 1, line 45, delete "Curr," and insert -- Curr. --, therefor.

In column 1, line 55, delete "Cell," and insert -- Cell. --, therefor.

In column 1, line 61, delete "Radiat," and insert -- Radiat. --, therefor.

In column 1, line 62, delete "Pathol," and insert -- Pathol. --, therefor.

In column 2, line 13, delete "$PFT_\alpha$" and insert -- $PFT_{-\alpha}$ --, therefor.

In column 2, line 17, delete "$PFT_\alpha$" and insert -- $PFT_{-\alpha}$ --, therefor.

In column 2, line 19, delete "$PFT_\alpha$" and insert -- $PFT_{-\alpha}$ --, therefor.

In column 3, line 50, delete "FIG. 1 depicts" and insert -- FIGS. 1A, 1B, 1C and 1D depict --, therefor.

UNITED STATES PATENT AND TRADEMARK OFFICE
CERTIFICATE OF CORRECTION

PATENT NO. : 6,696,441
APPLICATION NO. : 09/637531
DATED : February 21, 2004
INVENTOR(S) : Cottan et al.

Figure 2A:
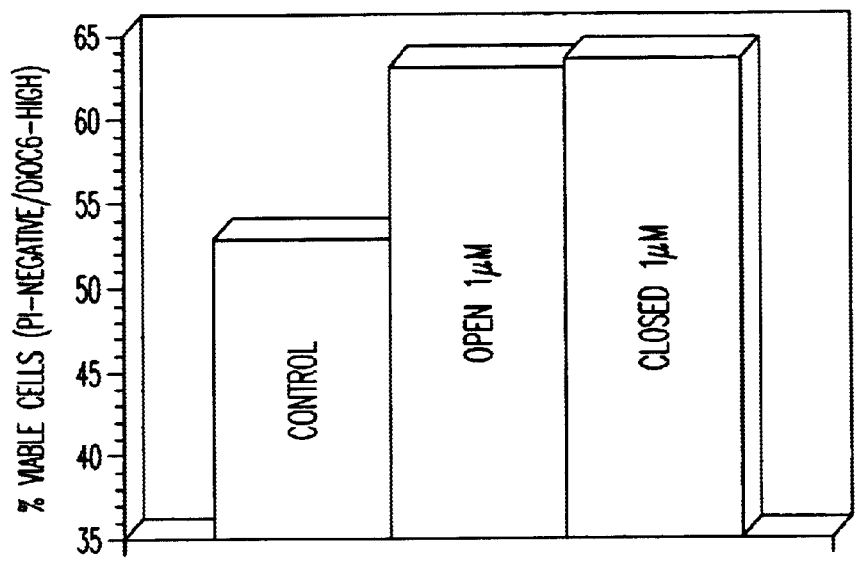
FIG. 2 depicts the protective effect of IBT against spontaneous apoptosis and against fludarabine-induced apoptosis.
Figure 2B:
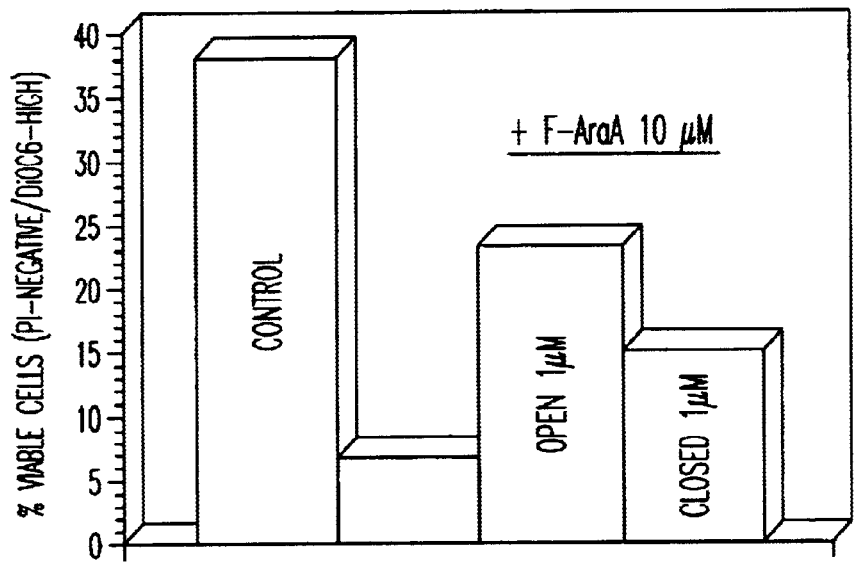

It is certified that error appears in the above-identified patent and that said Letters Patent is hereby corrected as shown below:

In column 3, line 52, delete "FIG. 2 depicts" and insert -- FIGS. 2A and 2B depict --, therefor.

In column 5, line 19, delete "$PFT_\alpha$" and insert -- $PFT_{-\alpha}$ --, therefor.

In column 6, line 18, delete "Khim, Pharm," and insert -- Khim. Pharm. --, therefor.

In column 6, line 22, delete "–$CH_2)_4$–" and insert - - –$(CH_2)_4$– - -, therefor.

In column 6, line 24, delete ")" before "(1999)".

In column 8, line 14, delete "gelation" and insert -- gelatin --, therefor.

In column 9, line 35, after "285" insert -- , --.

In column 10, line 29, delete "$PFT_\alpha$" and insert -- $PFT_{-\alpha}$ --, therefor.

In column 11, line 9, delete "DIOC6" and insert -- DiOC6 --, therefor.

Signed and Sealed this

Twenty-second Day of August, 2006

JON W. DUDAS
*Director of the United States Patent and Trademark Office*